United States Patent [19]

Goldstein et al.

[11] Patent Number: 5,022,409
[45] Date of Patent: Jun. 11, 1991

[54] ORAL RINSE IMMUNOGLOBULIN COLLECTION KIT FOR IMMUNOASSAY AND METHOD THEREOF

[75] Inventors: Andrew S. Goldstein, Portland; Thomas R. Thieme, Independence; Stefan Gavojdea, Tigard, all of Oreg.

[73] Assignee: Epitope, Inc., Beaverton, Oreg.

[21] Appl. No.: 410,401

[22] Filed: Sep. 21, 1989

[51] Int. Cl.⁵ .............................................. A61B 5/00
[52] U.S. Cl. .................................... 128/760; 206/569
[58] Field of Search ................. 128/760, 771; 424/52; 206/569, 570

[56] References Cited

U.S. PATENT DOCUMENTS

| | | | |
|---|---|---|---|
| 2,850,903 | 9/1958 | Schwerin | 128/771 |
| 4,114,605 | 9/1978 | McGhee et al. | 128/760 |
| 4,197,288 | 4/1980 | Snyder | 206/569 |
| 4,418,702 | 12/1983 | Brown et al. | 128/760 |
| 4,635,488 | 1/1987 | Kramer | 128/760 |
| 4,768,238 | 9/1988 | Kleinbey et al. | 128/760 |
| 4,774,962 | 10/1988 | Hebel et al. | 128/760 |
| 4,861,582 | 8/1989 | Pollock et al. | 424/52 |
| 4,932,081 | 6/1990 | Burns | 128/760 |

*Primary Examiner*—Max Hindenburg
*Attorney, Agent, or Firm*—Wegner, Cantor, Mueller & Player

[57] ABSTRACT

The present invention is concerned with collecting immunoglobulins from the oral cavity for immunological testing. A rinse is used to collect a specimen having a high concentration of immunoglobulins. The specimen can be subjected to a basic immunological testing technique which can be used as a tool for screening a patient for diseases. A test kit is also provided for.

10 Claims, 1 Drawing Sheet

ORAL RINSE IMMUNOGLOBULIN COLLECTION KIT FOR IMMUNOASSAY AND METHOD THEREOF

BACKGROUND OF THE INVENTION

The present invention relates to the field of immunological testing. In particular, a system for analyzing immunoglobulins extracted from the oral cavity is disclosed.

The immune system of the mouth not only interacts with the general immune system of the body, but also has its own centralized center for antigen-antibody response. Within the oral cavity is found extraoral lymph nodes and intraoral lymphoid aggregations. The extraoral lymph nodes are involved in the drainage of the oral mucosa, gum and teeth. However, the function of the intraoral lymphoid tissue is little understood.

The extraoral lymph nodes include a fine network of lymph capillaries which are superficially located in the mouth, palate, cheeks, lips, gingiva, and pulp of the teeth. The capillaries join to larger lymph vessels which originate from a network deep in the muscle of the tongue and other structures. An antigen can gain entry into the oral lymphatic system directly through the capillaries or be transported there by phagocytes. Once inside the network, the antigen can induce an immune response.

Included in the intraoral lymphoid tissue are generally four distinct tissue aggregations: (a) the tonsils, (b) scattered submucosal lymphoid aggregations, (c) salivary gland lymphoid tissue, and (d) gingival lymphoid tissue.

The tonsils (palatine and lingual) primarily produce B-cells and T-cells which are generally contained within a cap of lymphocytes and plasma cells. Antigen typically gains entry into the tonsils through a distinct epithelial region wherein the antigen can come into contact with the T- and B-cells to stimulate an immune response. The predominant type of antibody formed in the tonsils is found to be IgG followed, in order, by IgA, IgM, IgD and IgE.

Scattered submucosal lymphoid cells have not been extensively studied. These cell masses are histologically similar to tonsillar tissue.

Both the major salivary glands (parotid, submandibular and sublingual) and the minor salivary glands have been found to contain lymphocytes and plasma cells. Most of the plasma cells secrete IgA and some IgG or IgM. The IgA synthesized in the salivary glands has a dimeric structure. This type of IgA is referred to as secretory IgA (sIgA) and is the major immunoglobulin component in saliva.

Both T-cells and B-cells are found in the gingival lymphoid tissue. In subjects having clinically normal gingival tissue, T-cells predominate. During an infectionary period, such as during the development of gingivitis, B-cells have been found to predominate.

Plasma cells are also found in the gingival lymphoid tissue. Clusters of these cells are generally located near the blood vessels and predominately produce IgG. To a lesser extent, IgA and IgM are also manufactured. More importantly, Brandtzaeg et al. in, *Human Saliva: Clinical Chemistry and Microbiology* edited by Jorma O. Tenovuo, have shown that the immunoglobulins from the secretions from the gingival tissue area are directly related to the immunoglobulins found in the blood.

Because of the association between immunoglobulins of the blood and saliva, as well as the occurrence of sIgA peculiar to salival fluid, antigen-antibody tests have been conducted on the saliva to assess the value of such tests as a screening tool for diseases.

Collection of saliva from the salivary glands is complicated by the low volumes secreted, the diverse anatomic dispersion of the glands, and the relatively high viscosity of the fluid. Most techniques for collection involve the use of capillary tubes, suction into micropipettes, or aspiration into polypropylene syringes. These methods, however, are limited in that viscosity of the saliva makes the recovery of bubble-free material by these techniques difficult. Other methods of collection have been suggested to eliminate or at least reduce the quantity of bubbles in the sample. Among such methods include collecting saliva in the mouth by direct absorption with a sponge or flexible wad of osmotic membrane. After absorption, the saliva can be separated from the absorptive material by centrifugation or by compressing the absorptive material. However, absorption is generally accomplished by using cotton, nylon, or polyester as the absorptive material. These materials can non-specifically bind proteins which can result in an undesirably low recovery of immunoglobulins.

Testing of salivary specimens has not been extensively developed. In addition to problems with collection, the samples collected by the known methods typically contain about 0.01–0.1% of the immunoglobulin found in blood serum. Because of the reduced immunoglobulin content of saliva, it has been necessary to use more accurate antigen-antibody assay methods in screening patients for disease. Parry et al., "Rational Programme for Screening Travellers for Antibodies to Hepatitis A Virus", *The Lancet*, June 25, 1988, have discussed such methods and have found that the more accurate IgG-capture radioimmunoassay (GACRIA) test is preferable to avoid false indications which may occur in less accurate methods. Of course, more accurate testing procedures usually require added time and expense to achieve the test results.

BRIEF SUMMARY OF THE INVENTION

In order to eliminate or greatly reduce the problems inherent in antigen-antibody analysis of salival fluid, the present invention provides a method for collecting immunoglobulins from the oral cavity in a manner highly desirable for use in immunoassays. This method concerns rinsing the oral cavity with an aqueous solution, preferably a hypertonic solution, collecting the solution after rinsing and analyzing immunoglobulin content of the collected solution. Such a method results in a yield of immunoglobulins greater than would be expected and can incorporate basic antigen-antibody testing techniques as a screening tool for diseases.

The hypertonic solution of the present invention can also include additives to further provide for an optimal yield in salivary immunoglobulin content. Such additives can include compounds which maintain the correct pH, compounds which preserve the oral immunoglobulins, or compounds which inhibit the growth of organisms. The combination of such compounds results in a solution for collecting a salival fluid specimen which requires minimum manipulation in preparing the specimen for testing.

DETAILED DESCRIPTION OF THE INVENTION

Figure 1:
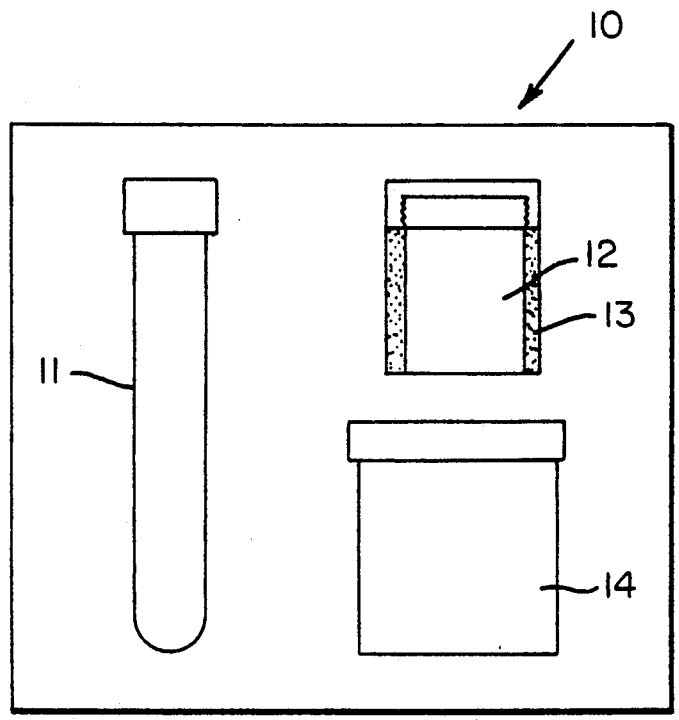
FIG. 1 is a top view of an immunological testing kit which includes the mouth rinse of this invention. The figure includes a section view of a receptacle 12.

The present invention is concerned with collecting salival fluid for immunological testing. A rinse is used to collect a specimen having a high concentration of immunoglobulins. High levels of immunoglobulins from the oral cavity are considered to be concentrations in excess of 50 µg total Ig per ml. The specimen can be subjected to a basic immunological testing technique which can be used as a tool for screening a patient for diseases.

The solution to be used as the rinse in the present invention is preferably a hypertonic solution. Although a non-hypertonic solution such as water may be used, it has been found that immunoglobulin production from salivation rapidly declines in concentration using such a solution. However, the use of a hypertonic solution results in a constant production of immunoglobulin from other sources within the oral cavity, those sources not being completely understood. By using a hypertonic solution, it is possible to gain an increase of as much as 8–16 times more immunoglobulin than by using distilled water.

A hypertonic solution is a salt solution which has an ionic strength exceeding that found in blood. In general, salts used in the preparation the hypertonic solution of the present invention are present in an amount of from about 1.5% to about 5% by weight, preferably 3.5%.

Salts which can be used in the preparation of the hypertonic solution include alkali metal compounds as well as alkaline earth metal compounds. Preferred salts include sodium chloride, potassium chloride, magnesium sulfate, magnesium chloride and calcium chloride. Sodium chloride is found to be the least toxic, least expensive and most palatable.

The hypertonic solution of the present invention can also include a compound or ingredient for stimulating salivation. The compounds capable of stimulating salivation are found to exhibit a sour taste. These compounds include weak organic acids. Preferred among the weak organic acids are citric acid, ascorbic acid and acetic acid. It is preferred to use citric acid and ascorbic acid at a concentration of between about 0.05% and 0.5%. The preferable range for acetic acid is between about 0.5% and 3.0%.

In order to minimize immunoglobulin degradation in a collected specimen, the hypertonic solution of the present invention can include a preservative. Such a preservative can act to inhibit proteolytic exzymatic activity which can be responsible for the destruction of antibody molecules. Compounds contemplated as a preservative include anti-bacterial agents, anti-fungal agents, bacteriostatic agents, fungistatic agents, and enzyme inhibitors. In a preferred embodiment, benzoic acid and sorbic acid are used as anti-fungal agents. As bacteriostatic agents, salts in high concentration and compounds capable of maintaining the hypertonic solution at low pH are contemplated. Such salts include thimersol, phenyl mercuric acetate, phenyl mercuric nitrate, and sodium azide. It is preferred to use these preservatives in a range of about 0.01% to about 0.2%.

To collect a specimen, the hypertonic solution is placed in the oral cavity and vigorously rinsed. The preferred volume of rinse is about 4–5 ml. Larger volumes further dilute the antibody, smaller volumes make it difficult to rinse vigorously. Generally, the longer the solution is rinsed, the greater the content of immunoglobulin in the specimen. Because of practical limitations, such as fatigue, it is difficult to rinse for more than two minutes. Rinsing time should be at least one minute and preferably two minutes. After rinsing is complete, the specimen is collected and made ready for testing.

The preferred solution has the following compositions:

| | |
|---|---|
| sodium chloride | 3.0% |
| citric acid | 0.2% |
| sodium benzoate | 0.05–0.1% |
| potassium sorbate | 0.05–0.1% |
| distilled water | |
| addition of 0.1 N sodium hydroxide to increase pH to 6.5 | |

The specimen can either be tested without further treatment or passed through a low protein binding filter. This filter will aid in removing particulates. A 5.0 micron filter is preferable. If the specimen is clear, a variety of immunological assays can be performed without further treatment. If the specimen is not clear, additional steps such as centrifugation (minimum of $400 \times g$ for 10 minutes) or filtering can be performed. Preferable immunological assays include enzyme-linked immunoabsorbent assay (ELISA) and Western Blot assay. These methods are particularly useful in determining the presence of antibody specific to Human Immunodeficiency Virus (HIV), Hepatitis A, Cytomegalovirus, Rubella, Herpes and Calicivirus.

The present invention also provides for a test kit such as that shown in FIG. 1. The test kit 10 preferably includes a mouth rinse tube 11 which contains the rinse solution of the present invention. For easy use, the rinse will be sterile and premixed in the mouth rinse tube. Preferably, the mouth rinse tube can contain about 4 ml of mouth rinse. The mouth rinse tube can also function to store the rinse after use in the mouth. However, a separate storage receptacle 12 for this function is desired. Additionally, the kit can contain an absorbent material 13 which is to be used when returning the used rinse to a lab for testing. For example, the storage receptacle can be wrapped in the absorbent material and then placed into a metal shipping container 14 which can also be included in the kit. The adsorbent material will then not only function to absorb any liquid on the outside of the storage receptacle, but will also act as a packing material to cushion the storage receptacle.

EXAMPLE 1

Oral Immunoglobulin Titers as a Function of Rinsing Time Samples or oral rinse are analyzed for total immunoglobulin content among thirteen normal individuals (i.e. seronegative for HIV antibody). Five of the individuals rinse for 10 seconds, four rinse for 30 seconds and four rinse for 60 seconds. A dot blot immunoassay is used to measure immunoglobulin. Each rinse sample is serially diluted and 1 microliter dots are placed on a after performing the immunoassay, indicates the approximate concentration of antibody in the undiluted rinse.

The results are as follows:

| SPECIMEN # | RINSE TIME (SECONDS) | ANTIBODY TITER IN RINSE (MICROGRAMS PER MILLITER) |
|---|---|---|
| 1 | 10 | 42 |
| 2 | 10 | 42 |
| 3 | 10 | 21 |
| 4 | 10 | 21 |
| 5 | 10 | 21 |
| 6 | 30 | 84 |
| 7 | 30 | 42 |
| 8 | 30 | 42 |
| 9 | 30 | 42 |
| 10 | 60 | 84 |
| 11 | 60 | 84 |
| 12 | 60 | 84 |
| 13 | 60 | 84 |

This study demonstrates that increasing rinse time results in greater concentrations of total immunoglobulin.

EXAMPLE 2

Western Blot Test for HIV Antibody—Comparing Serum, Whole Saliva and Rinse

A cohort of 15 individuals (7 seropositive, a seronegative) are compared for specific antibody levels in serum, whole saliva and rinse, using the Western Blot technique. This method shows the relative strength of antibody reaction against the major components of the AIDS virus (i.e., core, envelope, polymerase). The following results are obtained:

| PATIENT | SPECIMEN | SERO-STATUS | RELATIVE REACTION STRENGTH* |
|---|---|---|---|
| 166 | blood | (−) | (−) |
|  | saliva |  | (−) |
|  | rinse |  | (−) |
| 167 | blood | (−) | (−) |
|  | saliva |  | (−) |
|  | rinse |  | (−) |
| 168 | blood | (−) | (−) |
|  | saliva |  | (−) |
|  | rinse |  | (−) |
| 169 | blood | (+) | 3+ |
|  | saliva |  | 2+ |
|  | rinse |  | 4+ |
| 170 | blood | (+) | 4+ |
|  | saliva |  | +/− |
|  | rinse |  | 4+ |
| 171 | blood | (−) | (−) |
|  | saliva |  | (−) |
|  | rinse |  | (−) |
| 172 | blood | (+) | 3+ |
|  | saliva |  | 2+ |
|  | rinse |  | 4+ |
| 173 | blood | (+) | 2+ |
|  | saliva |  | +/− |
|  | rinse |  | 2+ |
| 174 | blood | (+) | 4+ |
|  | saliva |  | 3+ |
|  | rinse |  | 3+ |
| 175 | blood | (+) | 3+ |
|  | saliva |  | 4+ |
|  | rinse |  | 4+ |
| 176 | blood | (−) | (−) |
|  | saliva |  | (−) |
|  | rinse |  | (−) |
| 177 | blood | (−) | (−) |
|  | saliva |  | (−) |
|  | rinse |  | (−) |
| 178 | blood | (−) | (−) |
|  | saliva |  | (−) |
|  | rinse |  | (−) |
| 179 | blood | (+) | 1+ |
|  | saliva |  | 1+ |
|  | rinse |  | 1+ |
| 180 | blood | (−) | (−) |
|  | saliva |  | (−) |
|  | rinse |  | (−) |

*Relative reaction strength is defined as follows:
(−) = no bands visible by Western Blot;
+/− = 2 or fewer very weak bands visible;
1+ = 2 or more bands visible, at least 1 clearly;
2+ = 3 or more bands visible, at least 2 clearly;
3+ = all major bands visible, 1 or more weak;
4+ = all major bands strongly visible.

Data from Example 2 show that the rinse method of saliva collection is as effective as blood and more effective than whole saliva in detecting HIV antibodies in patient with AIDS. Patients without AIDS do not show any false positive results.

EXAMPLE 3

Anti-HIV Oral Antibody Stability—Water Versus EPI Rinse

The stability of oral-derived antibodies from an AIDS patient is tested by incubating samples derived by a distilled water rinse versus the Epitope formulation rinse. Western Blots are performed on both rinses after a five day storage of antibody at 37° C. Antibody from the distilled water rinse deteriorate from a 3+ to a +/− reaction after 14 days. Experiments measuring total immunoglobulin show similar results.

What is claimed is:

1. A method of collecting immunoglobulins for immunological testing comprising the steps of:
   (a) rinsing the oral cavity of a patient with a pharmaceutically acceptable hypertonic solution, wherein the hypertonic solution is in an effective concentration to recover a high concentration of immunoglobulin, and
   (b) collecting a specimen of the hypertonic solution after rinsing for analysis by immunological testing.

2. The method of claim 1, wherein the hypertonic solution is rinsed vigorously for a period of about two minutes.

3. The method of claim 1, wherein the hypertonic solution includes alkali metal salts or alkaline earth metal salts.

4. The method of claim 1, wherein the hypertonic solution includes a salival stimulating compound.

5. The method of claim 1, wherein the hypertonic solution includes a preservative.

6. The method of claim 1, wherein the hypertonic solution includes a microbicide.

7. An immunological method of testing comprising the steps of:
   (a) rinsing the oral cavity of a patient with a pharmaceutically acceptable hypertonic solution, wherein the hypertonic solution is in an effective concentration to recover a high concentration of immunoglobulins,
   (b) collecting a specimen of the hypertonic solution after rinsing, and
   (c) analyzing the specimen by enzyme-linked immunoabsorbent assay or Western Blot assay.

8. An immunological testing kit comprising a mouth rinse tube containing a sterile, premixed mouth rinse effective to recover a high concentration of immunoglobulin and a storage receptacle to store the mouth rinse after use in the mouth.

9. The immunological testing kit of claim 8, comprising absorbing material for absorbing liquid on the outside of the storage receptacle.

10. The immunological testing kit of claim 9, comprising a container for shipping the storage receptacle.

* * * * *